United States Patent [19]
Banko

[11] Patent Number: 5,800,448
[45] Date of Patent: Sep. 1, 1998

[54] ULTRASONIC SURGICAL INSTRUMENT

[75] Inventor: William Banko, New York, N.Y.

[73] Assignee: Surgical Design Corporation, Long Island City, N.Y.

[21] Appl. No.: 730,851

[22] Filed: Oct. 17, 1996

Related U.S. Application Data

[63] Continuation-in-part of Ser. No. 685,700, Jul. 24, 1996, abandoned.

[51] Int. Cl.$^6$ .................................................. A61B 17/32
[52] U.S. Cl. .......................................... 606/169; 606/174
[58] Field of Search ................................. 606/169, 174, 606/83, 170

[56] References Cited

U.S. PATENT DOCUMENTS

| | | | |
|---|---|---|---|
| 3,899,829 | 8/1975 | Storm et al. | 606/169 X |
| 3,990,452 | 11/1976 | Murry et al. | 606/169 |
| 5,275,607 | 1/1994 | Lo et al. | 606/169 |
| 5,522,830 | 6/1996 | Aranyi | 606/174 |

*Primary Examiner*—Michael H. Thaler
*Attorney, Agent, or Firm*—Darby & Darby

[57] ABSTRACT

A surgical cutting instrument is provided which includes a handpiece containing an ultrasonic transducer operative to convert electrical energy into ultrasonic longitudinal vibratory motion. A first elongate shaft has a first end operatively connected to the transducer and a second working end extending distally from the handpiece. A first cutting member is fixedly mounted to the working end of the first elongate shaft such that longitudinal vibratory motion generated by the transducer causes longitudinal vibratory motion of the first cutting member, via the first elongate shaft. A second cutting member is pivotally mounted to a nodal point on the working end of the first shaft and is pivotable between an open position and a closed position with respect to the first cutting member. A second shaft has a first end pivotally connected to the second cutting member for affecting pivotable movement of the second cutting member between the open and closed position.

29 Claims, 3 Drawing Sheets

ULTRASONIC SURGICAL INSTRUMENT

BACKGROUND OF THE INVENTION

1. Field of the Invention

This application is a continuation-in-part application for Ser. No: 08/685,700 filed Jul. 24, 1996, which application has been abandoned.

The present invention relates to surgical instrumentation for cutting and coagulating tissue. More particularly, the present invention relates to ultrasonic surgical scissors for cutting and coagulating tissue with a single vibrating blade member.

2. Discussion of the Related Art

Various types of ultrasonic vibrating surgical instruments for cutting and coagulating tissue are known. For example, see U.S. Pat. No. : 5,322,066 to Davison et al.; U.S. Pat. No. 5,275, 607 to Lo et al. and U.S. Pat. No. 3,702,948 to Balamuth.

Such prior art vibratory surgical instrumentation typically include a handpiece formed with a stack of laminations to which is connected an acoustic impedance transformer. At least one surgical cutting blade member is connected to the acoustic impedance transformer. A housing is provided which fits around the laminations and at least around a portion of the acoustic impedance transformer. The housing often has embedded therein the coils for converting the electrical energy into magnetic energy. The magnetic energy is then applied to magnetostrictive nickel laminations.

In general, the major direction of vibration of the acoustic impedance transformer is longitudinal of the length of the handpiece. When the housing is attached to the transducer, it is often desirable to attach it at a nodal point on the acoustic impedance transformer to reduce the amount of energy which is transmitted from the transformer to the housing and to reduce the heat generated.

As compared with laser surgery and electrosurgery, which essentially use heat to cause hemostasis, a vibratory surgical instrument converts electrical energy to reciprocating mechanical motion. The reciprocating mechanical motion is transmitted to a cutting blade member, via a coupling member, whereby the vibrating blade member cuts and coagulates tissue. A noted advantage associated with ultrasonic surgical cutting instruments includes rapid cutting and hemostasis of tissue without the risk of damaging adjacent tissues by stray laser light or arching electrical current, which is commonly associated with laser surgery and electrosurgery techniques. Thus, there is no char, smoke or odor to contaminate or obstruct the surgical field.

But an associated disadvantage of ultrasonic cutting instruments is it is often difficult to precisely manipulate the vibrating blade members at the surgical site. This is because the vibrating blade members not only vibrate along the longitudinal axis of the instrument, but often vibrate along differing axis tangential to the longitudinal axis of the instrument. These tangential vibrations render precise manipulation difficult at the often sensitive surgical site.

Therefore, it is an object of the present invention to provide an improved vibratory surgical instrumentation which overcomes the above noted drawbacks.

SUMMARY OF THE INVENTION

The subject invention relates to vibratory surgical instrumentation for cutting and coagulating tissue. In particular, the surgical cutting instrument in accordance with the subject invention is provided with a handpiece containing an ultrasonic transducer operative to convert electrical energy into ultrasonic longitudinal vibratory motion. Extending from the handpiece is an elongate portion including a fixed outer tubular member depending from the handpiece. An inner shaft is received in the fixed outer tubular member for coaxial reciprocating movement relative to the fixed outer tubular member. A proximal end portion of the inner shaft is operatively connected to the transducer for causing the inner shaft to longitudinally vibrate.

A first cutting member is fixedly mounted to the distal end of the inner shaft and extends distally from the distal end of the outer tubular member. Longitudinal vibratory motion generated by the transducer affects corresponding longitudinal vibratory motion of the first cutting member, via the inner shaft.

A second cutting member is pivotally connected to a nodal point region on the inner shaft and is pivotable between an open and closed position with respect to the vibrating first cutting member. A second shaft has a first end pivotally connected to the second cutting member for affecting pivotable movement of the second cutting member between the open and closed positions.

BRIEF DESCRIPTION OF THE DRAWINGS

Further features of the present invention will become readily apparent from the following detailed description of the invention taken in conjunction with the accompanying drawings, in which.

DETAILED DESCRIPTION OF THE PREFERRED EMBODIMENT

Figure 1:
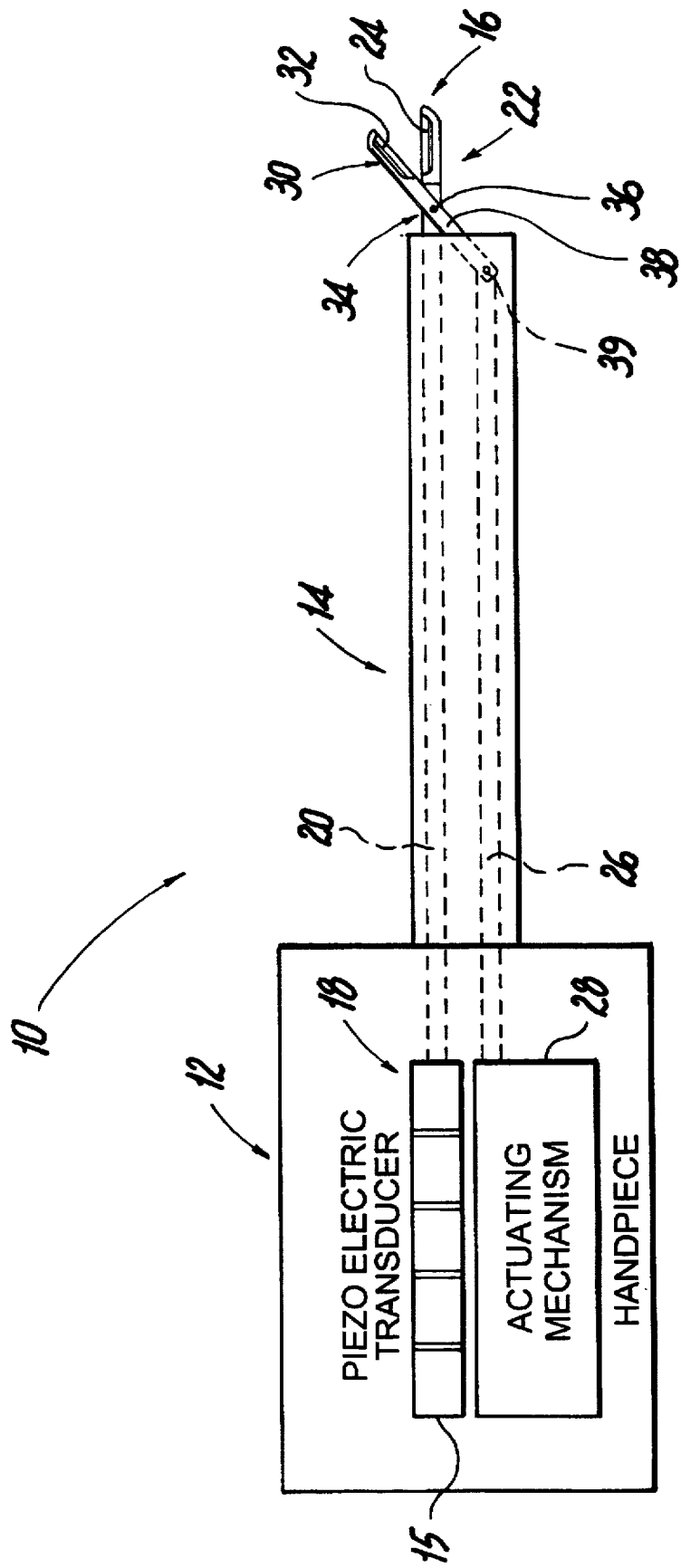
FIG. 1 is a diagrammatic illustration of a vibratory surgical instrument in accordance with the subject invention.

The surgical instrument 10 of the subject invention is illustrated in FIG. 1. Since the surgical instrument 10 of the subject invention is intended to be implemented in a wide variety of surgical instrumentation (e.g., vascular, endoscopic, laparoscopic, etc.), for ease of illustration, the subject invention surgical instrument 10 will be described in conjunction with the simplified diagrammatic illustration of FIG. 1. But it is to be appreciated that the subject invention surgical instrument may be adapted to be implemented in any one of a wide variety of surgical instrumentation. Further, it is to be appreciated that the subject invention surgical instrument is compact, lightweight and easy to use. It is intended to enable the surgeon to use the instrument with one hand, thus freeing the other hand for performance of other surgical tasks.

With reference to FIG. 1, the subject invention surgical instrument 10 includes a handpiece 12 having a fixed outer tubular member 14 extending distally therefrom. A pair of cooperating blade (e.g, scissor) members 16 are located in proximity to the distal end of outer tubular member 14. The handpiece 12 houses a transducer 18, preferably an ultrasonic transducer. The transducer 18 may consist of any suitable means for converting an electrical signal into mechanical longitudinal vibration. For example, the transducer 18 may include a piezoelectric 15 (see FIG. 1). Further, the transducer 18 may consist of a stack of laminations of a suitable material, such as Nickel (see FIG. 3). The laminations 13 are connected together at the proximal end of the handpiece 12 and are connected at its distal end to one end of an acoustic impedance transformer (not shown). The acoustic impedance transformer is a body of metal of suitable shape and thickness necessary to convert the vibrations of the laminations into longitudinal motion. The other end of the acoustic impedance transformer is preferably attached to a fixed scissor member for providing longitudinal motion thereof. Such a lamination transducer is described in commonly assigned U.S. Pat. No. 5,417,203, the disclosure of which is hereby incorporated by reference.

The surgical instrument 10 includes a reciprocating shaft 20, which is slidably received for longitudinal movement in outer tubular member 14. The proximal end of reciprocating shaft 20 is operatively connected to transducer 18.

The distal end of reciprocating shaft 20 extends distally from the open distal end of tubular member 14. The generated longitudinal vibrations of transducer 18 causes longitudinal vibratory motion of reciprocating shaft 20. A first scissor member 22 having cutting surface 24 is fixedly connected to the distal end of shaft 20. Reciprocating shaft 20 is operational to transmit the generated longitudinal vibratory motion of transducer 18 to the first scissor member 22.

An elongate actuating shaft 26 is preferably coaxially slidably received (preferably in parallel relationship to reciprocating shaft 20) in outer tubular member 14 for reciprocating longitudinal motion therein. But it is to be appreciated that elongate actuating shaft 26 is not to be limited to be slidably mounted within tubular member 14, but rather it may be slidably mounted outside of tubular member 14. The proximal end portion of actuating shaft 14 extends into handpiece 12 and is operatively connected to an actuating mechanism 28. Actuating mechanism 28 is operatively associated with handpiece 12 and is preferably located within handpiece 12, as shown in FIG. 1.

Actuating mechanism 28 is operational to affect reciprocating longitudinal motion of actuating shaft 26 relative to the fixed outer tubular member 14. Actuating mechanism 28 may consist of any suitable mechanism for affecting longitudinal movement of actuating shaft 26. The actuating mechanism 28 can be manually or automatically driven. It is to be appreciated that actuating mechanism 28 may consist of a manually operated handle member with squeeze type or lever depression actuation, pneumatic piston linear drivers, and electrical motors of direct current or solenoid drive.

Figure 2:
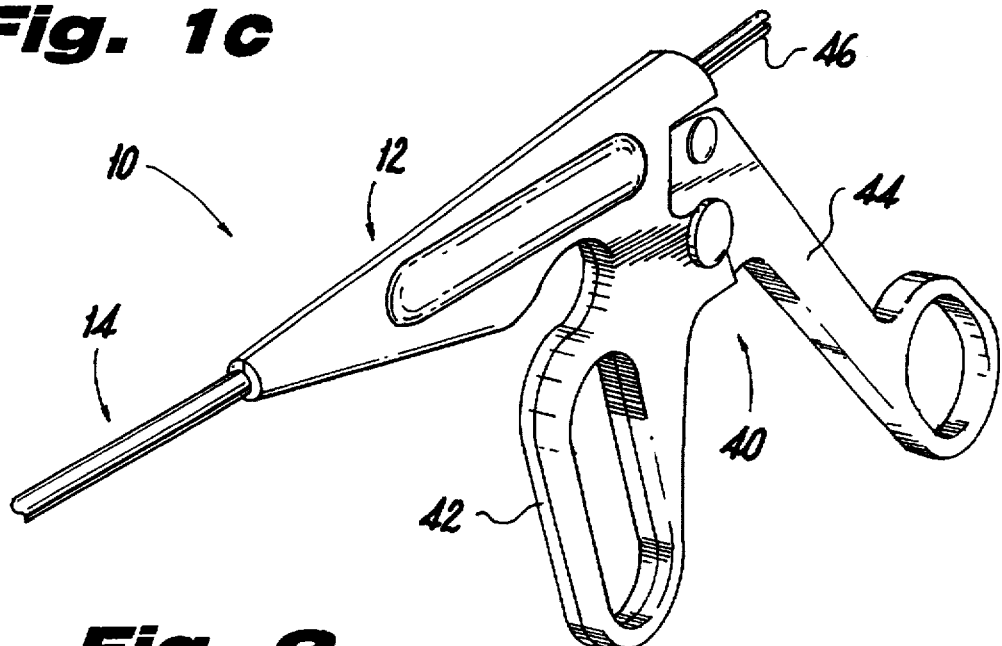
FIG. 2 is a perspective view of a surgical instrument having a handle assembly which embodies the subject invention of FIG. 1.

For example, and with reference to FIG. 2, actuating mechanism 28 is shown on handpiece 12 to consist of a manually operated handle assembly 40 having a fixed handle 42 and a pivoting handle 44. Within a cavity of the handle assembly 40, the proximal end portion of the reciprocating shaft 20 is operatively connected to a transducer 18 motion of pivoting handle 44 affects corresponding reciprocating longitudinal motion of actuating shaft 26 relative to outer tubular member 14. Further illustrated is a plug member 46 extending from the handpiece 12 for providing the transducer 18 (mounted within the cavity of handpiece 12) with electrical connection to an outside electrical source.

With returning reference to FIG. 1, the distal end portion of actuating shaft 26 extends distally from outer tubular member 14 and is operatively connected to a pivoting second scissor member 30 having cutting surface 32. The second scissor member 30 is preferably mounted at a pivoting assembly 34 located on the distal end portion of the reciprocating shaft 20. The pivoting assembly 34 is preferably located at a nodal point on the reciprocating shaft 20 to reduce vibrations occurring along the longitudinal axis of the reciprocating shaft 20 providing more controlled cutting action between the first and second scissor member 22, 30 when the first scissor member 22 is caused to vibrate longitudinally, particularly at an ultrasonic rate.

Figure 1A:
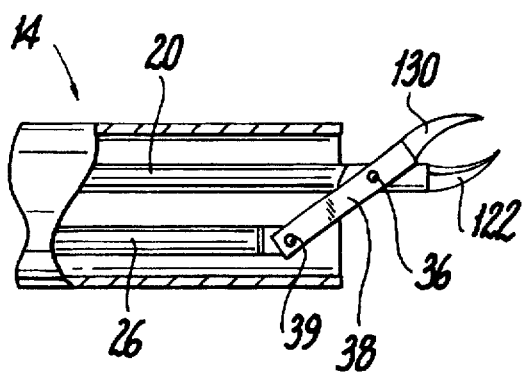
FIGS. 1a and 1b illustrate alternative embodiments of curved scissor members attached to the surgical instrument of FIG. 1.
Figure 1B:
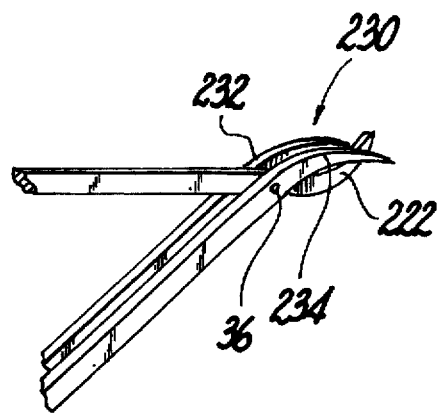
Figure 1C:
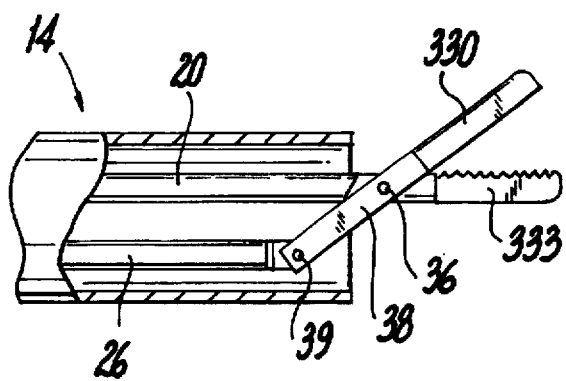
FIG. 1c illustrates an alternative embodiment of a serrated scissor member attached to the surgical instrument of FIG. 1.

Preferably, the proximal end portions of the first and second scissor members 22, 30 each define a through-hole configured to slidably receive a pivot pin 36 for pivotally connecting the first and second scissors members 22, 30 to each other. But it is to be appreciated that any suitable assembly for pivotally connecting the first and second scissor members 22, 30 may be implemented in the subject invention surgical instrument 10. For example, the pivoting assembly 34 may consist of a yoke assembly. It is to be further appreciated that the structural configuration of each of the first and second scissor members 22, 30 is not to be limited to the embodiment shown in FIG. 1, but rather may encompass any type of structural configuration for use in surgical procedures. For instance, and as is shown in FIG. 1a, the first and second scissor members 122, 130 may be configured to be cooperatively curved toward each other for encapsulating tissue during a cutting procedure, thereby preventing tissue from escaping from the cutting region of the scissor members during a surgical procedure. Referring now to FIG. 1b, another embodiment of the scissor members for surgical instrument 10 is shown. In this embodiment, the second scissor member 230 includes first and second curved blade members 232, 234, which are preferably parallel to one another. The first and second blade members 232, 234 are spaced a sufficient distance apart from one another for reception of the first scissor member 222 therebetween. This embodiment is particularly advantageous for retaining the encapsulated tissue at a cutting point on the first scissor member 222 during a cutting procedure. Thus, the first and second blade members 232, 234 of the second scissor member 230 prevents tissue from skewing or sliding from the first scissor member 222 during a surgical procedure. Yet another embodiment of the scissor members 322, 330 for surgical instrument 10 is shown in FIG. 1c wherein at least one of the blade members 324, 332 (e.g., blade member 324) is provided a serrated cutting edge. Hence, the serrated cutting edge 324 enables sawing cutting action surgical instrument 10.

As shown in FIG. 1, the proximal end portion of the second scissor member 30 is operatively connected to one end of a coupling shaft 38 with the other end of the coupling shaft 38 being pivotally connected to the distal end portion of the actuating shaft 26. Preferably, a second pivot pin 39 pivotally connects the distal end portion of actuating shaft 26 to coupling shaft 38. Thus, reciprocating longitudinal movement of actuating shaft 26 affects corresponding pivotable movement of the second scissor member 30 relative to the fixed first scissor member 22, via coupling shaft 38. For example, if the actuating mechanism 28 consists of the manually handle assembly 40, as shown in FIG. 2, actuation of the actuating mechanism 28 is affected through the transfer of movement to the pivoting handle member 44. Movement of the pivoting handle member 44 causes reciprocating longitudinal movement of the actuating shaft 26 causing the second scissor member 30 to pivot between the open and closed position relative to the first scissor member 22.

In use of the subject invention surgical instrument 10, the pivoting movement of the second scissor member 30 towards the first scissor member 22 causes the cutting and coagulating of tissue positioned therebetween, while the ultrasonic longitudinal reciprocating motion of the first and second scissor members 22, 30 greatly enhances the cutting and coagulating of the tissue. It is to be appreciated that the above described surgical instrument in accordance with the subject invention may be utilized for cutting very hard and dense connective tissue, ligaments and cartilage.

Figure 3:
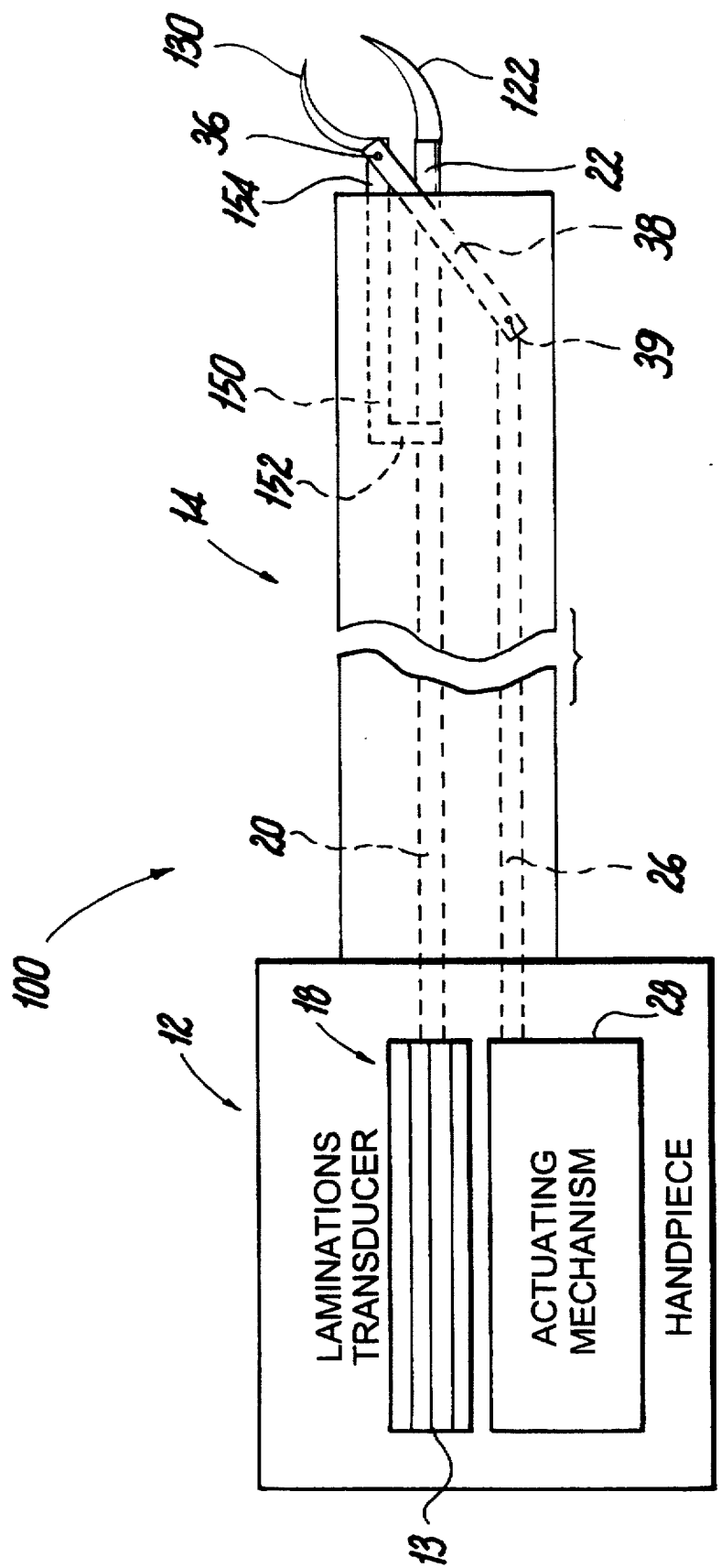
FIG. 3 is a diagrammatic illustration of an alternative embodiment of a vibratory surgical instrument in accordance with the subject invention.

Referring now to FIG. 3, an alternative embodiment of the subject surgical instrument 100 is shown and will be described below. Surgical instrument 100 is substantially similar to the surgical instrument 10 shown in FIG. 1 and described above, wherein like reference numerals identify like elements. Surgical instrument 100 differs from surgical instrument 10 in that it includes a nodal extension member 150 connected at a nodal point region on reciprocating shaft 20, which is a region of little or no longitudinal or axial motion. The nodal extension member 150 may be connected to reciprocating shaft 20 by any known attaching means, such as welding or screwing. As discussed above, nodal points of the reciprocating shaft 20 are points at which little or no vibrations occur. The nodal extension member 150 is preferably an L-shaped member of a predetermined length, but it is to be appreciated that it may be of any suitable configuration and dimension. In particular, nodal extension member 150 must be of a configuration such that the longitudinal axis of nodal extension member 150 is offset in a different plane from the plane containing the longitudinal axis of reciprocating shaft 20.

Preferably, nodal extension member 150 extends within the outer tubular member 14, with the distal end portion 154 of the nodal extension member 150 extending distally from outer tubular member 14. Fixedly connected to the distal end portion 22 of reciprocating shaft 20 is the first scissor member 122. As described above in conjunction with FIG. 1, the second scissor member 130, operatively connected to the actuating shaft 26, via the coupling shaft 38, is pivotally mounted to the distal end portion 154 of the nodal extension member 150 so as to move between an open and closed position relative to the first scissor member 122. Operation of the surgical instrument 100 is identical to the surgical instrument 10 of FIG. 1 (as described above), whereby reciprocating longitudinal movement of the actuating shaft 26 causes the second scissor 130 to pivot between the open and closed positions relative to the first scissor member 122.

The provision of the nodal extension member 150 is advantageous in that it permits the nodal point of shaft 20 to be effectively distally extended from the handpiece 12 of the surgical instrument. Since a reciprocating shaft 20 often only has one nodal point, it may often be the scenario where the nodal point of the shaft 20 is positioned in too close of proximity to the handpiece 12 to pivotally connect scissor members thereto to accomplish a specific surgical procedure, such as endoscopic surgery. Therefore, by connecting a nodal extension member 150 to the nodal point of the shaft 20, the effective working end of the instrument 100 mounting the first and second scissor members 122, 130 (i.e., the distal end 154 of the extension member 150) is positioned at a sufficient distance away from the handpiece 12 needed to accomplish a specific surgical task.

Although the subject invention has been described with emphasis on a particular embodiment for a surgical cutting instrument, it should be understood that the figures are for illustration of an exemplary embodiment of the subject invention and should not be taken as limitations or thought to be the only means of carrying out the subject invention. For example, the subject invention surgical cutting instrument may be miniaturized and utilized in vascular surgery or inserted through a small incision, and with fiber optic guidance, can cut damaged or unwanted tissue (e.g., for performing surgery on the collateral or the semilunar cartilage in the knee). Further, it is contemplated that many changes and modifications may be made to the subject invention without departing from the spirit and scope of the invention as disclosed above.

What is claimed is:

1. A surgical instrument comprising:
   a handpiece;
   a transducer mounted in the handpiece, the transducer being operative to convert electrical energy into longitudinal vibratory motion;
   a first elongate shaft having a first end operatively connected to the transducer and a second end extending distally from the handpiece;
   a first cutting member fixedly mounted to the second end of the first shaft such that longitudinal vibratory motion generated by the transducer causes longitudinal vibratory motion of the first cutting member;
   a second cutting member pivotally mounted in proximity to the second end of the first shaft the second cutting member being pivotable between an open and closed position with respect to the first cutting member; and
   a second shaft having a first end pivotally connected to the second cutting member for affecting pivotable movement of the second cutting member between the open and closed positions.

2. A surgical instrument as recited in claim 1, wherein the transducer is operative to convert electrical energy into ultrasonic longitudinal vibratory motion.

3. A surgical instrument as recited in claim 1, wherein the transducer includes a stack of laminations for converting electrical energy into longitudinal vibratory motion.

4. A surgical instrument as recited in claim 1, wherein the transducer includes a piezoelectric for converting electrical energy into longitudinal vibratory motion.

5. A surgical instrument as recited in claim 1, further including a pivoting assembly for pivotally mounting the second cutting member to the second end of the first shaft, the pivoting assembly including a pivot pin, through holes formed in the first and second cutting members slidably receive the pivot pin.

6. A surgical instrument as recited in claim 1, wherein the second cutting member is pivotally mounted to a nodal point on the first elongate shaft.

7. A surgical instrument as recited in claim 1, further including an actuating mechanism operatively associated with the handpiece and operatively connected to a second end of the second shaft for affecting longitudinal motion of the second shaft causing the second cutting member to move between the open and closed position.

8. A surgical instrument as recited in claim 1, wherein at least one of the first and second cutting members is provided with a serrated cutting edge.

9. A surgical instrument comprising:
   a handpiece;
   an elongate portion including a fixed outer tubular member depending from the handpiece, and an inner shaft received in the fixed outer tubular member for reciprocating movement with respect to the fixed outer tubular member;
   a transducer mounted in the handpiece, the transducer being operative to convert electrical energy into longitudinal vibratory motion, the transducer being operatively connected to a first end of the inner shaft for causing the inner shaft to longitudinally vibrate;

a first cutting member fixedly mounted to the second end of the inner shaft which extends distally from the outer tubular member such that longitudinal vibratory motion generated by the transducer causes longitudinal vibratory motion of the first cutting member;

a second cutting member pivotally mounted to the second end of the inner shaft, the second cutting member being pivotable between an open and closed position with respect to the first cutting member;

an actuating shaft having a first end pivotally connected to the second cutting member; and an actuating mechanism operatively associated with the handpiece and operatively connected to a second end of the actuating shaft for affecting longitudinal motion of the second shaft which causes the second cutting member to move between the open and closed positions.

10. A surgical instrument as recited in claim 9, wherein the transducer is operative to convert electrical energy into ultrasonic longitudinal vibratory motion.

11. A surgical instrument as recited in claim 10, wherein the transducer includes a stack of laminations for converting electrical energy into longitudinal vibratory motion.

12. A surgical instrument as recited in claim 11, wherein the transducer includes a piezoelectric for converting electrical energy into longitudinal vibratory motion.

13. A surgical instrument as recited in claim 9, further including a pivoting assembly for pivotally mounting the second cutting member to the second end of the inner shaft, the pivoting assembly including a pivot pin configured to slidably receive through holes formed in the first and second cutting members.

14. A surgical instrument as recited in claim 13, wherein the second cutting member is pivotally mounted to a nodal point on the inner shaft.

15. A surgical instrument as recited in claim 9, wherein the actuating mechanism includes a pivoting handle member pivotally mounted to the handpiece and operatively connected to the second end of the actuating shaft such that pivotable movement of the handle member affects longitudinal motion of the actuating shaft.

16. A surgical instrument as recited in claim 9, wherein at least one of the first and second cutting member is provided with a serrated cutting edge.

17. A surgical instrument comprising:

a handpiece having a fixed handle and a pivoting handle;

an elongate portion including a fixed outer tubular member depending from the handpiece, and an inner shaft slidably received in the fixed outer tubular member for reciprocating movement with respect to the fixed outer tubular member;

an ultrasonic transducer mounted in the handpiece, the transducer being operative to convert electrical energy into longitudinal vibratory motion, the transducer being operatively connected to a first end of the inner shaft for causing the inner shaft to longitudinally vibrate;

a first cutting member fixedly mounted to a second end of the inner shaft which extends distally from the outer tubular member such that longitudinal vibratory motion of the inner shaft causes longitudinal vibratory motion of the first cutting member;

a second cutting member pivotally mounted to the second end of the inner shaft, the second cutting member being pivotable between an open and closed position with respect to the first cutting member; and an actuating shaft slidably received in the fixed outer tubular member having a first end pivotably connected to the second cutting member and a second end operatively connected to the pivoting handle such that movement of the pivoting handle affects longitudinal motion of the actuating shaft which causes the second cutting member to move between the open and closed positions.

18. A surgical instrument as recited in claim 17, wherein the transducer includes a stack of laminations for converting electrical energy into ultrasonic longitudinal vibratory motion.

19. A surgical instrument as recited in claim 17, wherein the transducer includes a piezoelectric for converting electrical energy into ultrasonic longitudinal vibratory motion.

20. A surgical instrument comprising:

a handpiece;

a transducer mounted in the handpiece, the transducer being operative to convert electrical energy into longitudinal vibratory motion;

a first elongate shaft having a proximal end operatively connected to the transducer and a distal end extending distally from the handpiece, the first elongate shaft defining a longitudinal axis;

an extension member having a proximal end connected to a nodal point at the distal end of the first elongate shaft, the extension member having a longitudinal axis that is offset from the longitudinal axis of the first elongate shaft;

a first cutting member fixedly mounted to the distal end of the first elongated shaft such that longitudinal vibratory motion generated by the transducer causes longitudinal vibratory motion of the first cutting member;

a second cutting member pivotally mounted in the distal end of the extension member, the second cutting member being pivotable between an open and closed position with respect to the first cutting member; and a second shaft having a distal end pivotally connected to the second cutting member for affecting pivotable movement of the second cutting member between the open and closed positions.

21. A surgical instrument as recited in claim 20, wherein the extension member is L-shaped.

22. A surgical instrument as recited in claim 20, wherein the transducer includes a stack of laminations for converting electrical energy into longitudinal vibratory motion.

23. A surgical instrument as recited in claim 20, wherein the transducer includes a piezoelectric for converting electrical energy into longitudinal vibratory motion.

24. A surgical instrument as recited in claim 20, further including a pivoting assembly for pivotally mounting the second cutting member to the distal end of the first shaft, the pivoting assembly including a pivot pin configured to slidably receive through holes formed in the first and second cutting members.

25. A surgical instrument as recited in claim 20, further including an actuating mechanism operatively associated with the handpiece and operatively connected to a proximal end of the second shaft for affecting longitudinal motion of the second shaft causing the second cutting member to move between the open and closed position.

26. A surgical instrument as recited in claim 25, wherein the actuating mechanism includes a pivoting handle member pivotally mounted to the handpiece and operatively connected to the second end of the actuating shaft such that pivotable movement of the handle member affects longitudinal motion of the actuating shaft.

27. A surgical instrument as recited in claim 20, wherein the first and second scissor members are curved.

28. A surgical instrument as recited in claim 27, wherein the second scissor member includes first and second blade members spaced substantially parallel and at a distance apart from one another for reception of the first scissor member therebetween.

29. A surgical instrument as recited in claim 20, wherein at least one of the first and second cutting members is provided with a serrated cutting edge.

* * * * *